United States Patent
Dey et al.

(10) Patent No.: US 9,718,775 B2
(45) Date of Patent: Aug. 1, 2017

(54) OXINDOLE COMPOUNDS AND COMPOSITIONS COMPRISING THE SAME

(71) Applicant: MILLIKEN & COMPANY, Spartanburg, SC (US)

(72) Inventors: Sanjeev K. Dey, Spartanburg, SC (US); Eduardo Torres, Boiling Springs, SC (US); Suchitra Datta, Spartanburg, SC (US); Mary E. Mason, Moore, SC (US); Philip G. Harris, Spartanburg, SC (US)

(73) Assignee: Milliken & Company, Spartanburg, SC (US)

( * ) Notice: Subject to any disclaimer, the term of this patent is extended or adjusted under 35 U.S.C. 154(b) by 0 days.

(21) Appl. No.: 14/613,910

(22) Filed: Feb. 4, 2015

(65) Prior Publication Data
US 2015/0259287 A1   Sep. 17, 2015

Related U.S. Application Data

(60) Provisional application No. 61/953,168, filed on Mar. 14, 2014.

(51) Int. Cl.
*C07D 209/34* (2006.01)
*C08K 5/3417* (2006.01)

(52) U.S. Cl.
CPC .......... *C07D 209/34* (2013.01); *C08K 5/3417* (2013.01)

(58) Field of Classification Search
CPC ............................ C07D 209/34; C08K 5/3417
See application file for complete search history.

(56) References Cited

U.S. PATENT DOCUMENTS

| | | | | |
|---|---|---|---|---|
| 6,964,977 B2 * | 11/2005 | Harris | ................ | A61K 31/4045 514/339 |
| 7,250,442 B2 * | 7/2007 | Brown | ................ | C07D 209/34 514/415 |
| 8,088,816 B2 | 1/2012 | Halperin et al. | | |

FOREIGN PATENT DOCUMENTS

| | | |
|---|---|---|
| JP | 2008-39883 A | 2/2008 |
| WO | WO 80/01566 A1 | 8/1980 |
| WO | WO 2006/065829 | 6/2006 |
| WO | WO 2006/136606 A2 | 12/2006 |
| WO | WO 2013/022765 A1 | 2/2013 |

OTHER PUBLICATIONS

Altman, et al., "Orthogonal Pd- and Cu-Based Catalyst Systems for C- and N-Arylation of Oxindoles", J. Am. Chem. Soc. 2008, 130, 9613-9620.
Basavaiah et al., "Toward understanding the scope of Baylis-Hillman reaction: synthesis of 3-(2-hydroxyphenyl)indolin-2-ones and polycyclic fused furans", Tetrahedon 66 (2010) pp. 5612-5622.
Durban et al., "Palladium-Catalyzed A-Arylation of Oxindoles", Amer. Chem. Soc., Organic Letters 2008, vol. 10, No. 7, 1414-1415.111.
Hirose et al., "Studies on Benzoheterocyclic Derivatives. XIII. Synthesis and Pharmacological Actions of Indoline Derivatives", Chem. Pharm. Bull. 21 (5), pp. 960-971 (1973).
Hossain et al., "Antioxidant Potential Study of Some Synthesized N-heterocycles", Bandladesh Med. Res. Counc. Bull 2009, 35, 49-52.
Hossain et al., "In Vitro Free Radical Scavenging Activity of Some β-Lactams and Phenolics", International Journal of Pharmacy and Pharmaceutical Sciences vol. 2, Issue 2, 2010, pp. 60-63.
Kuethe, et al., "Vinylogous Pummerer Reaction of Amido-Substituted Sulfoxides as a Method for Preparing Oxindoles and Tetrahydroisoquinolones", J. Org. Chem. 1995, 60, 7082-7083.
Nieto et al., "Superefectrophilic Activation of N-Substituted Isatins: Implications for Polymer Synthesis, a Theoretical Study", Macromol.Theory Simul. 2009, 18, 138-144.
Niwa et al. "Oxidative Reaction of Oxindole-3-acetic Acids", Biosci, Biotechnol. Biochem., 67 (9), 1870-1874, 2003.
Salim et al., "Rauniticine-alio-Oxindole B and Rauniticinic-allo Acid B, New Heteroyohimbine-Type Oxindole Alkaloids from the Stems of Malaysian *Uncaria longiflora* var. *pteropoda*", Molecules 2011, 16, 6541-6548.
Trost et al., "Catalytic Double Stereoinduction in Asymmetric Allylic Alkylation of Oxindoles", Chem. Eur. J. 2010, 16, 296-303.
Yu et al., "Highly Site-Selective Direct C—H Bond Functionalization of Phenols with A-Aryl-A-diazoacetates and Diazooxindoles via Gold Catalysis", J. Am. Chem. Soc. 2014, 136, 6904-6907.
Xie et al., "Facile Synthesis of Functionalized Spiropyrrolizidine Oxindoles via a Three-Component Tandem Cycloaddition Reaction", Moledules 2011, 16, 8745-8757.
Zhu et al., "Actual Structure, Thermodynamic Driving Force, and Mechanism of Benzofuranone-Typical Compounds as Antioxidants in Solution", J. Phys. Chem. 8, 2011, 115, 3588-3603.
Chemical Abstracts Service Database Accession No. 93729-59-0, Abstract of Compound with the Registry No. 993729-59-0, Dec. 18, 1984.
PCT/US2015/014998 International Search Report, International filing date Feb. 9, 2015, 5 pages.
PCT/US2015/014998 Written Opinion of the International Searching Authority, International filing date Feb. 9, 2015, 9 pages.

* cited by examiner

*Primary Examiner* — Golam M M Shameem
(74) *Attorney, Agent, or Firm* — Robert M. Lanning

(57) ABSTRACT

Compounds that are derivatives of oxindole conform to the general structure of Formula (I)

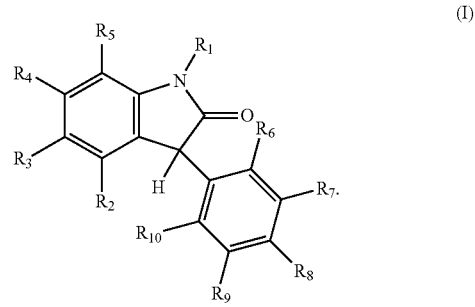

(I)

These compounds are believed to exhibit antioxidant properties. A composition comprises an organic material and a compound conforming to the structure of Formula (I).

20 Claims, No Drawings

OXINDOLE COMPOUNDS AND COMPOSITIONS COMPRISING THE SAME

CROSS-REFERENCE TO RELATED APPLICATIONS

This application claims, pursuant to 35 U.S.C. §119(e), the benefit of the filing date of U.S. patent application No. 61/953,168, which was filed on Mar. 14, 2014.

TECHNICAL FIELD OF THE INVENTION

This application relates to compounds that are derivatives of oxindole (i.e., 2,3-Dihydro-1H-indol-2-one), particularly those that are substituted in the 3-position. The application also relates to compositions comprising such oxindole compounds.

BACKGROUND

Organic materials, such as polymers, are susceptible to degradation by oxidative species and exposure to electromagnetic radiation (e.g., infrared radiation, visible light, and ultraviolet light). Various compounds and compositions have been developed in order to combat this degradation of organic materials. These stabilizers function by various mechanisms. For example, one class of stabilizers protects against degradation by reacting with free radicals that are produced in the organic material. In the absence of a stabilizer, these free radicals can participate in reactions that degrade the organic material and produce additional free radicals that perpetuate the degradation. While stabilizers for organic materials are known, a need still remains for alternative compounds that can perform the stabilizing function and do not suffer from some of the deficiencies exhibited by existing stabilizers. This applications seeks to provide such improved stabilizer compounds.

BRIEF SUMMARY OF THE INVENTION

Generally, the invention provides compounds that are derivatives of oxindole conforming to the structure of Formula (I)

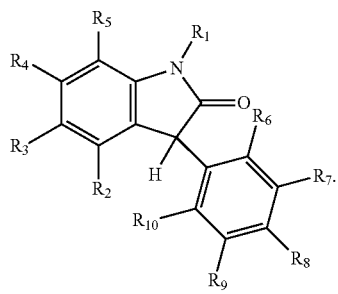

(I)

Applicants believe that these compounds exhibit antioxidant properties due to the ability of the lactam to form a free radical at the 3-position by loss of the hydrogen atom. It is believed that this enables the compounds to scavenge free radicals and inhibit oxidation of certain materials, such as organic materials. Accordingly, Applicants believe that these properties make the compounds suitable for use in stabilizing organic materials from degradation. Further, Applicants have discovered that the compounds can be substituted with a variety of substituents in order to modify their reactivity and/or compatibility with different materials.

In a first embodiment, the invention provides a compound conforming to the structure of Formula (I)

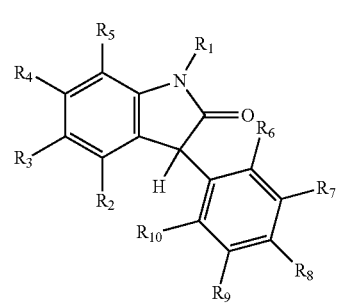

(I)

wherein $R_1$ is selected from the group consisting of hydrogen, alkyl groups, hydroxyalkyl groups, alkoxyalkyl groups, aryl groups, and $R_{20}$; $R_2$, $R_3$, $R_4$, and $R_5$ are independently selected from the group consisting of hydrogen, halogen atoms, alkyl groups, hydroxyalkyl groups, alkoxy groups, and aryl groups; $R_6$, $R_7$, $R_8$, $R_9$, and $R_{10}$ are independently selected from the group consisting of hydrogen, alkyl groups, alkoxy groups, aryl groups, $R_{14}$, $R_{15}$, —$SR_{16}$, —$NR_{17}R_{18}$, and —$OR_{20}$; provided if $R_1$ is selected from the group consisting of hydrogen, alkyl groups, hydroxyalkyl groups, alkoxyalkyl groups, aryl groups, alkanoyl groups, alkenoyl groups, and aryloyl groups, then at least one of $R_6$, $R_7$, $R_8$, $R_9$, and $R_{10}$ is selected from the group consisting of $R_{14}$, $R_{15}$, —$SR_{16}$, —$NR_{17}R_{18}$, and —$OR_{20}$; $R_{14}$ is a group conforming to the structure of Formula (II)

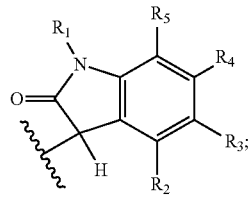

(II)

$R_{15}$ is a group conforming to the structure of Formula (III)

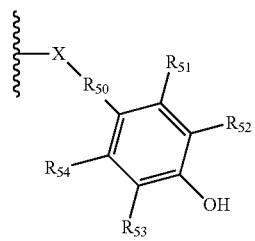

(III)

X is selected from the group consisting of —N(H)—, —O—C(O)—, and —N(H)—C(O)—; $R_{50}$ is selected from the group consisting of a bond and alkanediyl groups; $R_{51}$, $R_{52}$, $R_{53}$, and $R_{54}$ are independently selected from the group consisting of hydrogen and alkyl groups; $R_{16}$ is selected from the group consisting of hydrogen, alkyl groups, hydroxyalkyl groups, alkoxyalkyl groups, aryl groups, $R_{19}$, and $R_{20}$; $R_{19}$ is a group conforming to a structure selected from the group consisting of Formula (IVA), (IVB), and (IVC)

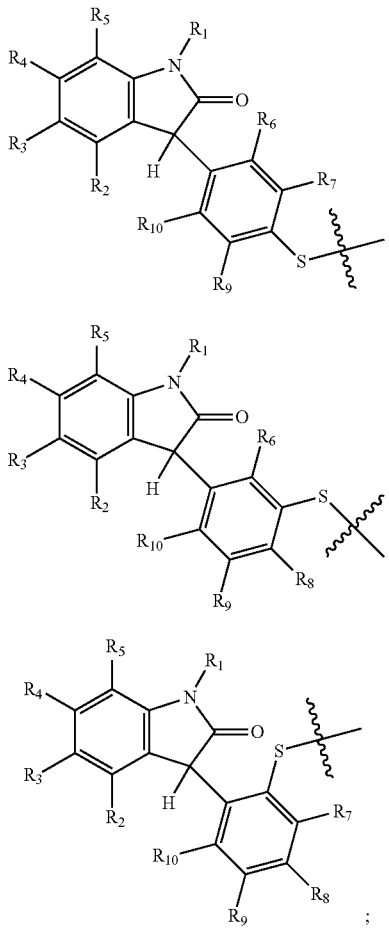

(IVA)

(IVB)

(IVC)

$R_{17}$ and $R_{18}$ are independently selected from the group consisting of hydrogen, alkyl groups, hydroxyalkyl groups, alkoxyalkyl groups, aryl groups, and $R_{20}$; and $R_{20}$ is selected from the group consisting of:
(a) alkanoyl groups, alkenoyl groups, and aryloyl groups;
(b) —$R_{21}$—O—$R_{22}$, where $R_{21}$ is selected from the group consisting of alkanediyl groups, and $R_{22}$ is selected from the group consisting of alkyl groups, alkanoyl groups, alkenoyl groups, and aryloyl groups;
(c) groups conforming to the structure of Formula (V)

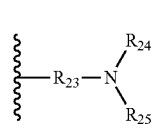

(V)

where $R_{23}$ is selected from the group consisting of alkanediyl groups, $R_{24}$ and $R_{25}$ are independently selected from the group consisting of hydrogen, alkyl groups, —$R_{21}$—O—$R_{22}$, —$R_{30}$—O—$R_{31}$—$R_{32}$, and —$R_{31}$—$R_{32}$;
(d) —$R_{30}$—O—$R_{31}$—$R_{32}$, where $R_{30}$ is selected from the group consisting of alkanediyl groups; and (e) —$R_{31}$—$R_{32}$, where $R_{32}$ is selected from the group consisting of hydrogen, alkyl groups, alkanoyl groups, alkenoyl groups, and aryloyl groups; and $R_{31}$ is a divalent substituent selected from the group consisting of:
(i) divalent substituents comprising two or more divalent repeating units independently selected from repeating units conforming to the structure of Formula (C)

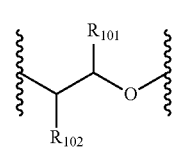

(C)

wherein $R_{101}$ and $R_{102}$ are independently selected from the group consisting of hydrogen, alkyl, hydroxyalkyl, aryl, alkoxyalkyl, and aryloxyalkyl;
(ii) divalent substituents conforming to the structure of Formula (CX)

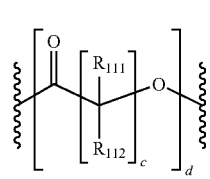

(CX)

wherein $R_{111}$ and $R_{112}$ are independently selected from the group consisting of hydrogen, hydroxyl, and $C_1$-$C_{10}$ alkyl, c is an integer from 1 to 12, and d is a positive integer;
(iii) divalent substituents conforming to the structure of Formula (CXX)

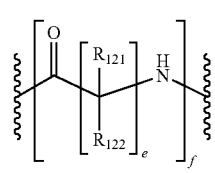

(CXX)

wherein $R_{121}$ and $R_{122}$ are independently selected from the group consisting of hydrogen, hydroxyl, and $C_1$-$C_{10}$ alkyl, e is an integer from 1 to 12, and f is a positive integer;
(iv) divalent substituents conforming to the structure of Formula (CXXX)

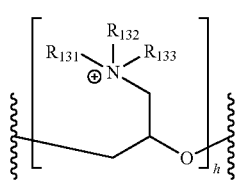

(CXXX)

wherein $R_{131}$, $R_{132}$, and $R_{133}$ are independently selected from alkyl and hydroxyalkyl, and h is a positive integer; and (v) divalent substituents comprising two or more substituents selected from the group consisting of substituents conforming to a structure of Formula (C), (CX), (CXX), or (CXXX).

In a second embodiment, the invention provides a composition comprising an organic material and a compound conforming to the structure of Formula (I)

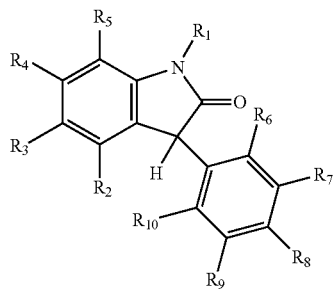

(I)

wherein $R_1$ is selected from the group consisting of hydrogen, alkyl groups, hydroxyalkyl groups, alkoxyalkyl groups, aryl groups, and $R_{20}$; $R_2$, $R_3$, $R_4$, and $R_5$ are independently selected from the group consisting of hydrogen, halogen atoms, alkyl groups, hydroxyalkyl groups, alkoxy groups, and aryl groups; $R_6$, $R_7$, $R_8$, $R_9$, and $R_{10}$ are independently selected from the group consisting of hydrogen, hydroxy, alkyl groups, alkoxy groups, aryl groups, $R_{14}$, $R_{15}$, —$SR_{16}$, —$NR_{17}R_{18}$, and —$OR_{20}$; $R_{14}$ is a group conforming to the structure of Formula (II)

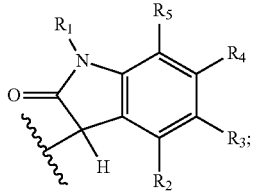

(II)

$R_{15}$ is a group conforming to the structure of Formula (III)

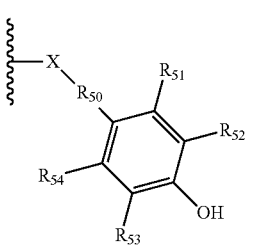

(III)

X is selected from the group consisting of —N(H)—, —O—C(O)—, and —N(H)—C(O)—; $R_{50}$ is selected from the group consisting of a bond and alkanediyl groups; $R_{51}$, $R_{52}$, $R_{53}$, and $R_{54}$ are independently selected from the group consisting of hydrogen and alkyl groups; $R_{16}$ is selected from the group consisting of hydrogen, alkyl groups, hydroxyalkyl groups, alkoxyalkyl groups, aryl groups, $R_{19}$, and $R_{20}$; $R_{19}$ is a group conforming to the structure of Formula (IVA), (IVB), or (IVC)

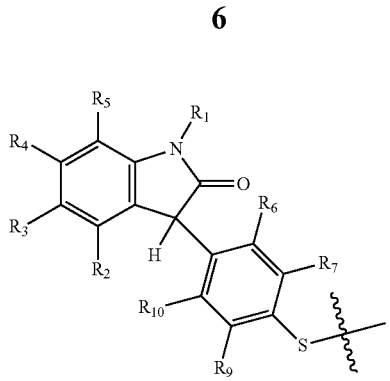

(IVA)

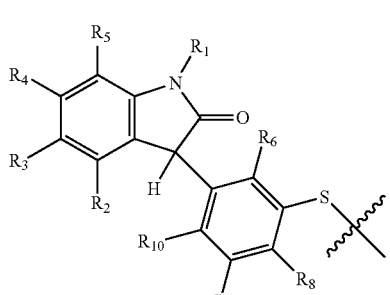

(IVB)

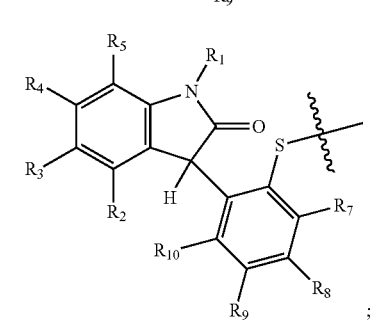

(IVC)

$R_{17}$ and $R_{18}$ are independently selected from the group consisting of hydrogen, alkyl groups, hydroxyalkyl groups, alkoxyalkyl groups, aryl groups, and $R_{20}$; and $R_{20}$ is selected from the group consisting of:

(a) alkanoyl groups, alkenoyl groups, and aryloyl groups;
(b) —$R_{21}$—O—$R_{22}$, where $R_{21}$ is selected from the group consisting of alkanediyl groups, and $R_{22}$ is selected from the group consisting of alkyl groups, alkanoyl groups, alkenoyl groups, and aryloyl groups;
(c) groups conforming to the structure of Formula (V)

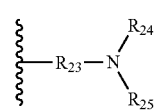

(V)

where $R_{23}$ is selected from the group consisting of alkanediyl groups, $R_{24}$ and $R_{25}$ are independently selected from the group consisting of hydrogen, alkyl groups, —$R_{21}$—O—$R_{22}$, —$R_{30}$—O—$R_{31}$—$R_{32}$, and —$R_{31}$—$R_{32}$;
(d) —$R_{30}$—O—$R_{31}$—$R_{32}$, where $R_{30}$ is selected from the group consisting of alkanediyl groups; and
(e) —$R_{31}$—$R_{32}$, where $R_{32}$ is selected from the group consisting of hydrogen, alkyl groups, alkanoyl groups, alkenoyl groups, and aryloyl groups; and $R_{31}$ is a divalent substituent selected from the group consisting of:

(i) divalent substituents comprising two or more divalent repeating units independently selected from repeating units conforming to the structure of Formula (C)

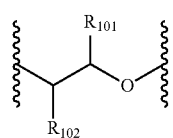
(C)

wherein $R_{101}$ and $R_{102}$ are independently selected from the group consisting of hydrogen, alkyl, hydroxyalkyl, aryl, alkoxyalkyl, and aryloxyalkyl;

(ii) divalent substituents conforming to the structure of Formula (CX)

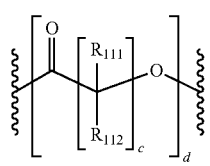
(CX)

wherein $R_{111}$ and $R_{112}$ are independently selected from the group consisting of hydrogen, hydroxyl, and $C_1$-$C_{10}$ alkyl, c is an integer from 1 to 12, and d is a positive integer;

(iii) divalent substituents conforming to the structure of Formula (CXX)

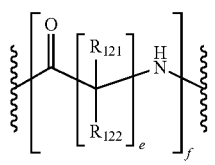
(CXX)

wherein $R_{121}$ and $R_{122}$ are independently selected from the group consisting of hydrogen, hydroxyl, and $C_1$-$C_{10}$ alkyl, e is an integer from 1 to 12, and f is a positive integer;

(iv) divalent substituents conforming to the structure of Formula (CXXX)

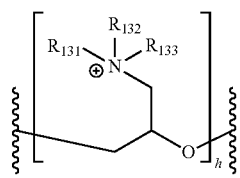
(CXXX)

wherein $R_{131}$, $R_{132}$, and $R_{133}$ are independently selected from alkyl and hydroxyalkyl, and h is a positive integer; and (v) divalent substituents comprising two or more substituents selected from the group consisting of substituents conforming to a structure of Formula (C), (CX), (CXX), or (CXXX).

DETAILED DESCRIPTION OF THE INVENTION

As used herein, the term "alkanoyl" refers to univalent functional groups derived from alkyl carboxylic acids by removal of a hydroxy group from a carboxylic acid group. In this definition, the term "alkyl carboxylic acids" refers to acyclic, unbranched and branched alkanes (including substituted alkanes) having one or more carboxylic acid groups. In this definition, the term "substituted alkanes" refers to compounds derived from acyclic unbranched and branched hydrocarbons in which (1) one or more of the hydrogen atoms of the hydrocarbon is replaced with a non-hydrogen atom (e.g., a halogen atom) or a non-alkyl functional group (e.g., a hydroxy group, aryl group, or heteroaryl group) and/or (2) the carbon-carbon chain of the hydrocarbon is interrupted by an oxygen atom (as in an ether), a nitrogen atom (as in an amine), or a sulfur atom (as in a sulfide).

As used herein, the term "alkenoyl" refers to univalent functional groups derived from alkenyl carboxylic acids by removal of a hydroxy group from a carboxylic acid group. In this definition, the term "alkenyl carboxylic acids" refers to acyclic, unbranched and branched olefins (including substituted olefins) having one or more carboxylic acid groups. In this definition, the term "substituted olefins" refers to compounds derived from acyclic, unbranched and branched hydrocarbons having one or more carbon-carbon double bonds in which (1) one or more of the hydrogen atoms of the hydrocarbon is replaced with a non-hydrogen atom (e.g., a halogen atom) or a non-alkyl functional group (e.g., hydroxy group, aryl group, heteroaryl group) and/or (2) the carbon-carbon chain of the hydrocarbon is interrupted by an oxygen atom (as in an ether) or a sulfur atom (as in a sulfide).

As used herein, the term "aryloyl" refers to univalent functional groups derived from aryl carboxylic acids by removal of a hydroxy group from a carboxylic acid group. In this definition, the term "aryl carboxylic acids" refers to arenes (including substituted arenes) having one or more carboxylic acid groups. In this definition, the term "substituted arenes" refers to compounds derived from monocyclic and polycyclic aromatic hydrocarbons in which one or more of the hydrogen atoms of the hydrocarbon is replaced with a non-hydrogen atom (e.g., a halogen atom) or a non-alkyl functional group (e.g., hydroxy group).

In a first embodiment, the invention provides a compound conforming to the structure of Formula (I)

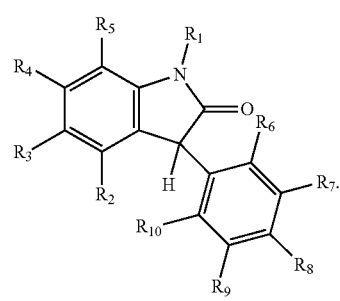
(I)

In the structure of Formula (I), $R_1$ is selected from the group consisting of hydrogen, alkyl groups, hydroxyalkyl groups, alkoxyalkyl groups, aryl groups, and $R_{20}$. $R_2$, $R_3$, $R_4$, and $R_5$ are independently selected from the group consisting of hydrogen, halogen atoms, alkyl groups, hydroxyalkyl groups, alkoxy groups, and aryl groups. $R_6$, $R_7$, $R_8$, $R_9$, and $R_{10}$ are independently selected from the group consisting of hydrogen, alkyl groups, alkoxy groups, aryl groups, $R_{14}$, $R_{15}$, —$SR_{16}$, —$NR_{17}R_{18}$, and —$OR_{20}$. In certain specific embodiments, if $R_1$ is selected from the group consisting of hydrogen, alkyl groups, hydroxyalkyl groups, alkoxyalkyl groups, aryl groups, alkanoyl groups, alkenoyl groups, and aryloyl groups, then at least one of $R_6$, $R_7$, $R_8$, $R_9$, and $R_{10}$ is selected from the group consisting of $R_{14}$, $R_{15}$, —$SR_{16}$, —$NR_{17}R_{18}$, and —$OR_{20}$.

$R_{14}$ is a group conforming to the structure of Formula (II)

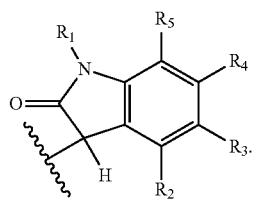

(II)

In the structure of Formula (II), $R_1$, $R_2$, $R_3$, $R_4$, and $R_5$ are independently selected from the groups recited above for such substituents in connection with Formula (I). The partial bond in the structure of Formula (II) (i.e., the bond truncated by the wavy line) represents the bond to a carbon atom in the aromatic ring in the structure of Formula (I). In one preferred embodiment, $R_1$, $R_2$, $R_3$, $R_4$, and $R_5$ of Formula (II) are the same as $R_1$, $R_2$, $R_3$, $R_4$, and $R_5$ of Formula (I).

$R_{15}$ is a group conforming to the structure of Formula (III)

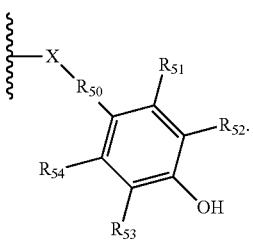

(III)

In the structure of Formula (III), X is selected from the group consisting of —N(H)—, —O—C(O)—, and —N(H)—C(O)—. $R_{50}$ is selected from the group consisting of a bond (i.e., a bond between the group represented by X and the carbon atom in the aromatic ring in the structure of Formula (III)) and alkanediyl groups. $R_{51}$, $R_{52}$, $R_{53}$, and $R_{54}$ are independently selected from the group consisting of hydrogen and alkyl groups. The partial bond in the structure of Formula (III) (i.e., the bond truncated by the wavy line) represents the bond to a carbon atom in the aromatic ring in the structure of Formula (I). In a preferred embodiment, X is —O—C(O)—, $R_{50}$ is a bond, $R_{51}$ and $R_{52}$ are hydrogen, and $R_{52}$ and $R_{53}$ are alkyl groups, with tert-butyl groups being particularly preferred.

$R_{16}$ is selected from the group consisting of hydrogen, alkyl groups, hydroxyalkyl groups, alkoxyalkyl groups, aryl groups, $R_{19}$, and $R_{20}$. $R_{19}$ is a group conforming to a structure selected from the group consisting of Formula (IVA), (IVB), and (IVC)

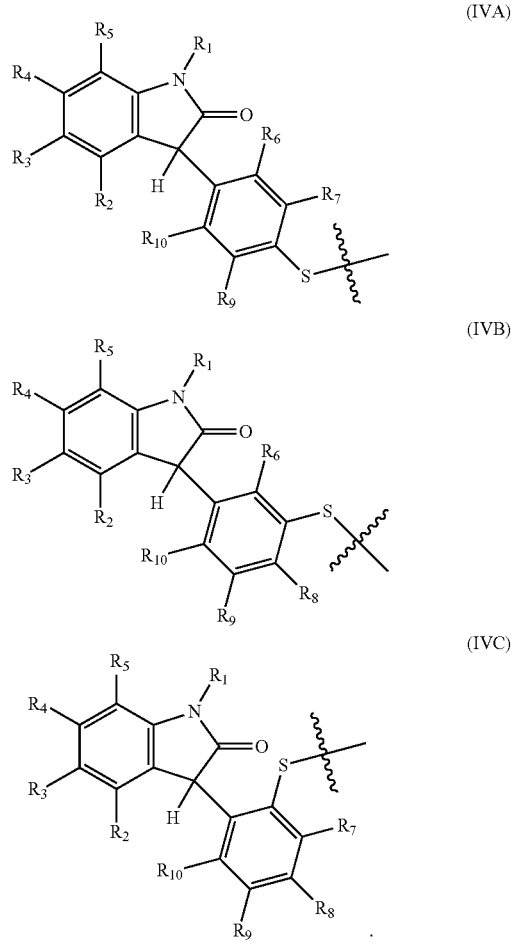

In the structures of Formulae (IVA), (IVB), and (IVC), $R_1$, $R_2$, $R_3$, $R_4$, $R_5$, $R_6$, $R_7$, $R_8$, $R_9$, and $R_{10}$ are independently selected from the groups recited above for such substituents in connection with the structure of Formula (I). The partial bond in the structures of Formulae (IVA), (IVB), and (IVC) (i.e., the bonds truncated by the wavy line) represents the bond between the sulfur atom in the structure of Formula (IVA), (IVB), or (IVC) and the sulfur atom in the group —$SR_{16}$. In a preferred embodiment, $R_1$, $R_2$, $R_3$, $R_4$, $R_5$, $R_6$, $R_7$, $R_8$, $R_9$, and $R_{10}$ in the structures of Formulae (IVA), (IVB), and (IVC) are the same as $R_1$, $R_2$, $R_3$, $R_4$, $R_5$, $R_6$, $R_7$, $R_8$, $R_9$, and $R_{10}$ for the structure of Formula (I).

$R_{17}$ and $R_{18}$ are independently selected from the group consisting of hydrogen, alkyl groups, hydroxyalkyl groups, alkoxyalkyl groups, aryl groups, and $R_{20}$. In a preferred embodiment, at least one of $R_{17}$ and $R_{18}$ is $R_{20}$.

$R_{20}$ is selected from the group consisting of (a) alkanoyl groups, alkenoyl groups, and aryloyl groups; (b) —$R_{21}$—O—$R_{22}$; (c) groups conforming to the structure of Formula (V); (d) —$R_{30}$—O—$R_{31}$—$R_{32}$; and (e) —$R_{31}$—$R_{32}$. In this group, $R_{21}$ is selected from the group consisting of alkanediyl groups, and $R_{22}$ is selected from the group consisting of alkyl groups, alkanoyl groups, alkenoyl groups, and aryloyl groups. The structure of Formula (V) is

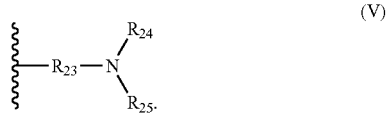

(V)

In the structure of Formula (V), $R_{23}$ is selected from the group consisting of alkanediyl groups, and $R_{24}$ and $R_{25}$ are independently selected from the group consisting of hydrogen, alkyl groups, $-R_{21}-O-R_{22}$, $-R_{30}-O-R_{31}-R_{32}$, and $-R_{31}-R_{32}$. $R_{30}$ is selected from the group consisting of alkanediyl groups, and $R_{32}$ is selected from the group consisting of hydrogen, alkyl groups, alkanoyl groups, alkenoyl groups, and aryloyl groups.

$R_{31}$ is a divalent substituent selected from the group consisting of:

(i) divalent substituents comprising two or more divalent repeating units independently selected from repeating units conforming to the structure of Formula (C)

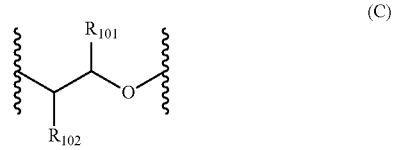

(C)

wherein $R_{101}$ and $R_{102}$ are independently selected from the group consisting of hydrogen, alkyl, hydroxyalkyl, aryl, alkoxyalkyl, and aryloxyalkyl;

(ii) divalent substituents conforming to the structure of Formula (CX)

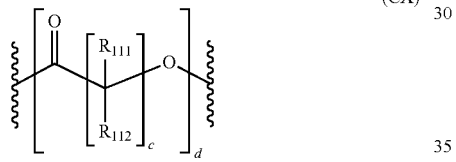

(CX)

wherein $R_{111}$ and $R_{112}$ are independently selected from the group consisting of hydrogen, hydroxyl, and $C_1$-$C_{10}$ alkyl, c is an integer from 1 to 12, and d is a positive integer;

(iii) divalent substituents conforming to the structure of Formula (CXX)

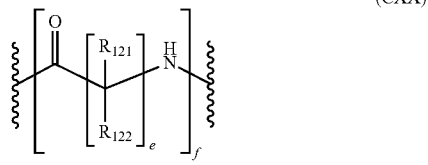

(CXX)

wherein $R_{121}$ and $R_{122}$ are independently selected from the group consisting of hydrogen, hydroxyl, and $C_1$-$C_{10}$ alkyl, e is an integer from 1 to 12, and f is a positive integer;

(iv) divalent substituents conforming to the structure of Formula (CXXX)

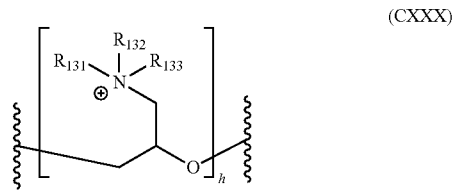

(CXXX)

wherein $R_{131}$, $R_{132}$, and $R_{133}$ are independently selected from alkyl and hydroxyalkyl, and h is a positive integer; and (v) divalent substituents comprising two or more substituents selected from the group consisting of substituents conforming to a structure of Formula (C), (CX), (CXX), or (CXXX).

In each of the structures outlined for $R_{31}$, the partial bonds (i.e., the bond truncated by the wavy line) represent bonds to adjacent portions of the compound, such as a bond to either the oxygen atom or $R_{32}$ in the group $-R_{30}-O-R_{31}-R_{32}$ or a bond to an adjacent divalent substituent selected from the recited group.

In a series of particularly preferred embodiments of the colorants, $R_{31}$ is a divalent substituent conforming to a structure of Formula (CI), (CII), or (CIII)

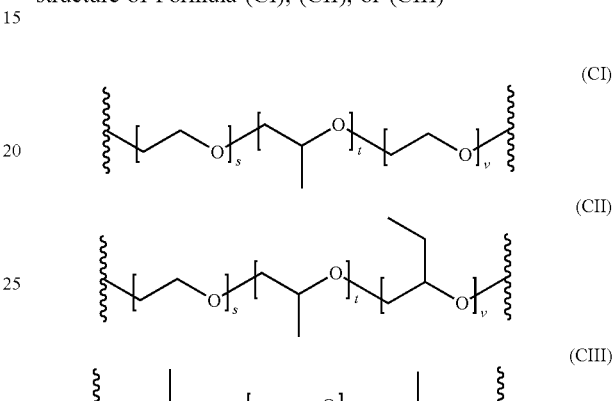

In the structures of Formulae (CI), (CII), and (CIII), s, t, and v are selected from the group consisting of zero and positive integers (e.g., 0 and integers from 1 to about 100); and the sum of s, t, and v is 2 or more (e.g., 2 to about 300, 3 to about 300, 2 to about 200, 3 to about 200, 2 to about 100, or 3 to about 100). In a preferred embodiment, the sum of s, t, and v is from 2 to about 50 or 3 to about 50. In another preferred embodiment, $R_{31}$ is a divalent substituent conforming to the structure of Formula (CI), s is an integer from 2 to about 50 (e.g., 3 to about 50), v is 0, and t is 0.

In the structures of Formulae (CI), (CII), and (CIII), the divalent substituent $R_{31}$ is depicted as comprising a series of repeating units arranged in a block configuration. While such an arrangement of the repeating units is possible and potentially preferred, the repeating units comprising the divalent substituent $R_{31}$ can also be arranged in a random configuration or in any suitable combination of a block configuration and a random configuration. For example, $R_{31}$ can be a divalent substituent comprising a series of two or more different repeating units conforming to the structure of Formula (C) arranged in a random configuration or a divalent substituent comprising a series of two more different repeating units conforming to the structure of Formula (C) and one or more repeating units conforming to the structure of Formula (CX) all arranged in a random configuration. Also, $R_{31}$ can be a divalent substituent comprising a series of two or more different repeating units conforming to the structure of Formula (C) arranged in a random configuration followed by a block of repeating units conforming to the structure of Formula (CX).

In one preferred specific embodiment, the invention provides a compound conforming to the structure of Formula (IA)

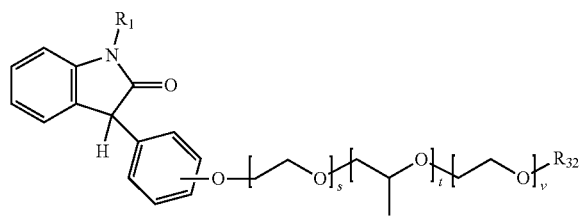

(IA)

In the structure of Formula (IA), $R_1$ is selected from the group consisting of hydrogen, aryl groups, alkanoyl groups, alkenoyl groups, and aryloyl groups. The oxygen atom initiating the alkyleneoxide chain can be attached to the phenyl ring in either the ortho, meta, or para position relative to the oxindole moiety, though preferably the oxygen atom is attached in either the meta or para position relative to the oxindole moiety. In a preferred embodiment, $R_1$ is hydrogen, and the oxygen atom initiating the alkyleneoxide chain is attached to the phenyl ring in either the meta or para position relative to the oxindole moiety. In another preferred embodiment, $R_1$ is an aryl group (e.g., a phenyl group), and the oxygen atom initiating the alkyleneoxide chain is attached to the phenyl ring in either the meta or para position relative to the oxindole moiety. In another preferred embodiment, $R_1$ is an alkanoyl group (e.g. acetyl group), and the oxygen atom initiating the alkyleneoxide chain is attached to the phenyl ring in either the meta or para position relative to the oxindole moiety.

In the structure of Formula (IA), the variables s, t, and v are selected from the group consisting of zero and positive integers (e.g., 0 and integers from 1 to about 100); and the sum of s, t, and v is 2 or more (e.g., 2 to about 300, 2 to about 200, or 2 to about 100). In a particularly preferred embodiment, s, t, and v are selected from the group consisting of zero and positive integers from 1 to about 50, with the sum of s, t, and v being from 2 to about 50. In this particular preferred embodiment, $R_{32}$ is selected from the group consisting of hydrogen, alkanoyl groups, and alkenoyl groups. In a particularly preferred embodiment, $R_{32}$ is hydrogen.

In one preferred specific embodiment, the invention provides a compound conforming to the structure of Formula (IB)

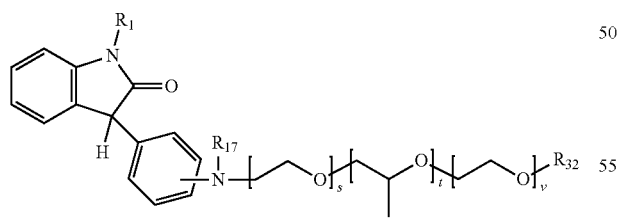

(IB)

In the structure of Formula (IA), $R_1$ is selected from the group consisting of hydrogen, aryl groups, alkanoyl groups, alkenoyl groups, and aryloyl groups. $R_{17}$ is selected from the groups recited above, with hydrogen, alkyl groups, —$R_{30}$—O—$R_{31}$—$R_{32}$, and —$R_{31}$—$R_{32}$ being particularly preferred. The nitrogen atom initiating the alkyleneoxide chain can be attached to the phenyl ring in either the ortho, meta, or para position relative to the oxindole moiety, though preferably the nitrogen atom is attached in either the meta or para position relative to the oxindole moiety. In a preferred embodiment, $R_1$ is hydrogen, and the nitrogen atom initiating the alkyleneoxide chain is attached to the phenyl ring in either the meta or para position relative to the oxindole moiety. In another preferred embodiment, $R_1$ is an aryl group (e.g., a phenyl group), and the nitrogen atom initiating the alkyleneoxide chain is attached to the phenyl ring in either the meta or para position relative to the oxindole moiety. In another preferred embodiment, $R_1$ is an alkanoyl group (e.g. acetyl group), and the nitrogen atom initiating the alkyleneoxide chain is attached to the phenyl ring in either the meta or para position relative to the oxindole moiety.

In the structure of Formula (IB), the variables s, t, and v are selected from the group consisting of zero and positive integers (e.g., 0 and integers from 1 to about 100); and the sum of s, t, and v is 2 or more (e.g., 2 to about 300, 2 to about 200, or 2 to about 100). In a particularly preferred embodiment, s, t, and v are selected from the group consisting of zero and positive integers from 1 to about 50, with the sum of s, t, and v being from 2 to about 50. In this particular preferred embodiment, $R_{32}$ is selected from the group consisting of hydrogen, alkanoyl groups, and alkenoyl groups. In a particularly preferred embodiment, $R_{32}$ is hydrogen.

The compounds of the invention can be made by any suitable process. For example, the compounds can be produced by reacting oxindole or an oxindole derivative (i.e., an oxindole derivative in which the 3-position remains unsubstituted) with an aryl halide, an aryl triflate, or an aryl tosylate in a variation of the Buchwald-Hartwig cross-coupling reaction. The oxindole or oxindole derivative used in the reaction preferably conforms to the structure of Formula (XX)

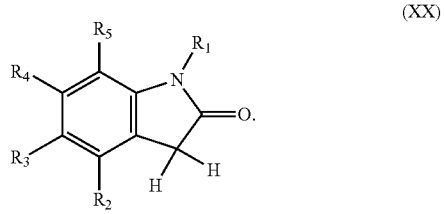

(XX)

In the structure of Formula (XX), $R_1$, $R_2$, $R_3$, $R_4$, and $R_5$ are independently selected from the groups recited above for such substituents in connection with Formula (I). The aryl halide, aryl triflate, or aryl tosylate preferably conforms to the structure of Formula (XXX)

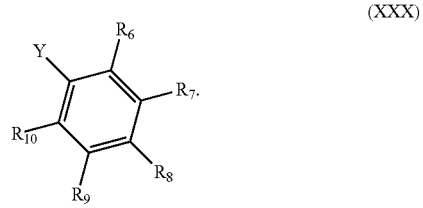

(XXX)

In the structure of Formula (XXX), Y is selected from the group consisting of Cl, Br, I, a triflate group (i.e., a trifluoromethanesulfonate group), and a tosyl group (i.e., a p-toluenesulfonyl group), and $R_6$, $R_7$, $R_8$, $R_9$, and $R_{10}$ are selected from the groups recited above for such substituents in connection with Formula (I). In order to produce those compounds in which one or more of $R_6$, $R_7$, $R_8$, $R_9$, and $R_{10}$ is $R_{14}$, the desired group (i.e., the group(s) from $R_6$, $R_7$, $R_8$, $R_9$, and $R_{10}$ that will be $R_{10}$) can replaced with another Y. For example, to produce a compound conforming to the structure of Formula (I) in which $R_8$ is $R_{14}$, the aryl halide, aryl triflate, or aryl tosylate can contain two Y groups, such as the compound conforming to the structure of Formula (XXXI)

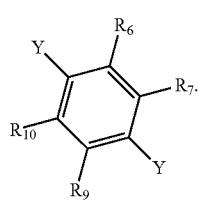

(XXXI)

An aryl halide, aryl triflate, or aryl tosylate compound having such a structure provides two reactive sites for the Buchwald-Hartwig cross-coupling reaction, which permits the compound to react with two molecules of the oxindole or oxindole derivative conforming to the structure of Formula (XX).

The reaction described in the preceding paragraphs can be performed under any suitable conditions. Typically, the Buchwald-Hartwig cross-coupling reaction is performed using a palladium catalyst in the presence of a base and a ligand. Suitable palladium catalysts include, but are not limited to, tris(dibenzylideneacetone)dipalladium(0). Suitable bases for the reaction include, but are not limited to, potassium carbonate. Suitable ligands for use in the reaction include, but are not limited to, XPhos (i.e., 2-Dicyclohexylphosphino-2',4',6'-triisopropylbiphenyl). The reaction can be performed in any suitable solvent, such as dioxane. The reaction typically is performed at elevated temperatures, such as about 100° C.

Applicants believe that one of the benefits to this route for synthesizing the compounds of the invention is that it permits a wide range of substitutions on the aromatic ring attached at the 3-position of the oxindole core. For example, one can easily synthesize aryl halides containing a variety of oligomeric or polymeric chains and, due to the flexibility of the Buchwald-Hartwig cross-coupling reaction, attach one of these aryl halides to the 3-position of the oxindole to produce a compound of the invention. This is believed to be superior to alternative methods for producing such oligomer or polymer-substituted compounds, which typically would proceed through an intermediate (i.e., a 3-aryl oxindole derivative) off which the oligomeric or polymeric chain is built. However, the range of possible oligomeric or polymeric chains that can be produced in this manner is limited because of possible side reactions between the oxindole core and the reactants used to build the oligomeric or polymeric chain.

In a second embodiment, the invention provides a composition comprising an organic material and a compound conforming to the structure of Formula (I). The compound conforming to the structure of Formula (I) used in the composition can be any of the compounds described above. In certain embodiments, more than one compound conforming to the structure of Formula (I) can be used.

The organic material in the composition can be any organic material that is susceptible to degradation resulting from exposure to electromagnetic radiation (e.g., infrared radiation, visible light, and/or ultraviolet light) or oxidative species. Suitable organic materials include, but are not limited to, hydrocarbon fuels, oils, waxes, greases, polymeric materials (e.g., thermoplastic polymers and thermoset polymers), and mixtures thereof.

The composition of the invention can comprise any suitable polymeric material or polymer. Generally, the polymer is a material that is susceptible to oxidative, thermal, and/or light-induced degradation and, therefore, in need of stabilization to prevent or retard such degradation. The polymer can be a natural, semisynthetic, or synthetic polymer or any suitable mixture of such polymers. The polymer can be a thermoset polymer or a thermoplastic polymer. The composition can also comprise any suitable mixture of one or more thermoset polymers and one or more thermoplastic polymers.

In one preferred embodiment of the composition, the polymer is a thermoplastic polymer. Suitable thermoplastic polymers include, but are not limited to, polyolefins (e.g., polyethylenes, polypropylenes, polybutylenes, and any combinations thereof), polyamides (e.g., nylon), polyurethanes, polyesters (e.g., polyethylene terephthalate), and the like, as well as any combinations thereof.

In one preferred embodiment of the composition, the polymer is a thermoplastic polymer selected from the group consisting of thermoplastic polyolefin polymers. In such an embodiment, the polymer can be any suitable thermoplastic polyolefin polymer, such as a polypropylene, a polyethylene, a polybutylene, and a poly(4-methyl-1-pentene). The composition can also comprise any suitable combination or mixture of such thermoplastic polymers. In a preferred embodiment, the thermoplastic polymer is a polyolefin selected from the group consisting of polypropylene homopolymers (e.g., atactic polypropylene, isotactic polypropylene, and syndiotactic polypropylene), polypropylene copolymers (e.g., polypropylene random copolymers), polypropylene impact copolymers, polyethylene, polyethylene copolymers, polybutylene, poly(4-methyl-1-pentene), and mixtures thereof. Suitable polypropylene copolymers include, but are not limited to, random copolymers made from the polymerization of propylene in the presence of a comonomer selected from the group consisting of ethylene, but-1-ene (i.e., 1-butene), and hex-1-ene (i.e., 1-hexene). In such polypropylene random copolymers, the comonomer can be present in any suitable amount, but typically is present in an amount of less than about 10 wt. % (e.g., about 1 to about 7 wt. %). Suitable polypropylene impact copolymers include, but are not limited to, those produced by the addition of a copolymer selected from the group consisting of ethylene-propylene rubber (EPR), ethylenepropylenediene monomer (EPDM), polyethylene, and plastomers to a polypropylene homopolymer or polypropylene random copolymer. In such polypropylene impact copolymers, the copolymer can be present in any suitable amount, but typically is present in an amount of from about 5 to about 25 wt. %.

In another preferred embodiment, the thermoplastic polymer can be a polyethylene. Suitable polyethylenes include, but are not limited to, low density polyethylene, linear low density polyethylene, medium density polyethylene, high density polyethylene, and combinations thereof. In certain preferred embodiments, the thermoplastic polymer is selected from the group consisting of medium density polyethylene, high density polyethylene, and mixtures thereof. In another possibly preferred embodiment, the thermoplastic polymer is a high density polyethylene.

In another preferred embodiment, the polymer is a thermoset polymer. In such an embodiment, the composition can comprise any suitable thermoset polymer. Suitable thermoset polymers include, but are not limited to, epoxies and polyurethane polymers. In a preferred embodiment, the organic material is a polyurethane polymer. In such an embodiment, the polyurethane polymer can be produced by the reaction of any suitable combination of polyols, polyisocyanates, chain extenders, and chain terminating agents.

Polyols suitable for use in making a polyurethane polymer include, but are not limited to, glycols of low molecular weight, such as ethylene glycol, 1,2-propylene glycol, 1,3-propylene glycol, 1,4-butylene glycol, and 1,6-hexamethylene glycol; polyester diols obtained from dibasic acids, such as adipic acid, maleic acid, and terephthalic acid; polyester diols, such as polylactones obtained by subjecting lactones to ring-opening polymerization with glycols; polycarbonate diols; and polyether diols, such as polytetramethylene glycol, polyethylene glycol, and polypropylene glycol.

Polyisocyanates suitable for use in making a polyurethane polymer include, but are not limited to, aromatic diisocyanates, such as toluene-2,4-diisocyanate (TDI), 4-methoxy-1,3-phenylene diisocyanate, 4-isopropyl-1,3-phenylene diisocyanate, 4-chloro-1,3-phenylene diisocyanate, 4-butoxy-1,3-phenylene diisocyanate, 2,4-diisocyanatodiphenyl ether, 4,4'-methylenebis(phenyl-isocyanate) (MDI), polymeric MDI, durylene diisocyanate, tolidine diisocyanate, xylylene diisocyanate (XDI), 1,5-naphthalene diisocyanate, benzidine diisocyanate, o-nitrobenzidine diisocyanate, and 4,4-diisocyanatodibenzyl; aliphatic diisocyanates, such as methylene diisocyanate, 1,4-tetramethylene diisocyanate, 1,6-hexamethylene diisocyanate, and 1,10-decamethylene diisocyanate; alicyclic diisocyanates, such as 1,4-cyclohexylene diisocyanate, 4,4-methylene-bis(cyclohexylisocyanate), 1,5-tetrahydronaphthalene diisocyanate, isophorone diisocyanate, hydrogenated MDI, and hydrogenated XDI; and polyurethane prepolymers obtained by reacting any of the aforementioned diisocyanates with polyols or polyamines of low molecular weights such that the resulting prepolymers have isocyanate groups at ends thereof. Among the aforementioned, aromatic diisocyanates, particularly diphenylmethane-4,4'-diisocyanate (4,4'-MDI) or polymeric MDI, are preferred for obtaining articles exhibiting good physical characteristics such as thermal stability, solution stability, and fracture strength. Alicyclic diisocyanates, such as isophorones, are preferred for obtaining polyurethanes that exhibit anti-yellowing properties and are not easily discolored upon exposure to sunlight.

Chain extenders suitable for use in making a polyurethane polymer include, but are not limited to, water; low-molecular diols, such as ethylene glycol and propylene glycol; aliphatic diamines, such as ethylenediamine; aromatic diamines, such as 4,4'-diaminodiphenylmethane; alicyclic diamines, such as 4,4'-diaminodicyclohexylmethane and isophoronediamine; alkanolamines, such as ethanolamine; hydrazines; and dihydrazides, such as succinic dihydrazide. Among the aforementioned chain extenders, the diamine compounds are preferable, with 4,4'-diaminodiphenylmethane being particularly preferred due to its heat resistance and 4,4'-diaminodicyclohexylmethane being preferred for light resistance. The aforementioned chain extenders can, of course, be used alone or in any suitable combination. Chain terminating agents suitable for use in making a polyurethane polymer include, but are not limited to, secondary amines, such as dibutylamine.

These reactants can be combined in any suitable manner to produce the polyurethane polymer. For example, the polyol, polyisocyanate, chain extender (if used), and chain terminating agent (if used) can be combined together into a single reactant mixture and reacted to yield the polyurethane polymer. Alternatively, the reactants can be sequentially reacted to yield the desired polymer. For example, the polyol and the polyisocyanate can be reacted first, with the subsequent addition of chain extender(s) and/or chain terminating agent(s). In such sequential reactions, it may be desirable to desirable to divide one reactant (e.g., the polyisocyanate) into multiple different additions. The reactant mixture can contain other reactants/agents used in the production of polyurethanes. For example, when a polyurethane foam is desired, the reactant mixture can contain a blowing agent, such as water.

When the organic material is a thermoset polymer, the compounds of the invention can be incorporated into the polymer in two ways. First, the compounds can be simply dispersed within the thermoset polymer. This type of incorporation results when the compound does not possess functional groups that are reactive to the components used to make the thermoset polymer. Second, when the compound possesses functional groups that are capable of reacting with the components used to make the thermoset polymer, the compound can be incorporated into the molecular structure of the thermoset polymer. While not wishing to be bound to any particular theory, it is believed that incorporating the compound into the molecular structure of the thermoset polymer may be advantageous because it can prevent the compound from leaching or migrating out of the thermoset polymer. Also, it is believed that incorporating the compound into the molecular structure of the thermoset polymer ensures that the compound is more evenly distributed within the polymer and is therefore better able to stabilize the entire polymer from degradation.

As briefly noted above, the compound can be incorporated into the molecular structure of the thermoset polymer when it comprises functional groups that are reactive to the components used to make the thermoset polymer. For example, when the thermoset polymer is a polyurethane polymer, a compound possessing one or more active hydrogen atoms will react with the polyisocyanate and become incorporated into the polymer's molecular structure. If the compound possesses only one active hydrogen atom, the compound will react with only one polyisocyanate molecule and terminate the propagation of the polymer chain at the point where it reacted and was attached to the chain. If the compound possesses two or more active hydrogen atoms, the compound can react with multiple polyisocyanate molecules and be incorporated into the polymer chain without terminating the propagation of the polymer chain. In this context, the term "active hydrogen" is utilized herein to refer to a hydrogen atom that is bonded to an atom that is more electronegative than carbon. Suitable active hydrogen-containing groups include, but are not limited to, a hydroxy group, primary and secondary amine groups, amide groups, and sulfhydryl groups (e.g., thiols). In an embodiment where the polymer is a polyurethane polymer and the compound is reacted into the molecular structure of the polymer, the compound preferably comprises at least one hydroxy group as the active hydrogen-containing group. More preferably, the compound comprises at least two hydroxy groups.

In similar manner to the case of polyurethane polymers, a compound possessing one or more active hydrogen atoms can react with an epoxy resin and become incorporated into the epoxy's molecular structure. In such an embodiment, the active hydrogen atom(s) can be present in any suitable active-hydrogen containing group including those listed above. In an embodiment where the polymer is an epoxy and the compound is reacted into the molecular structure of the epoxy, the compound preferably comprises at least one amine group (more preferably a primary amine group) as the active hydrogen-containing group. More preferably, the compound comprises at least two amine groups (more preferably at least two primary amine groups).

The compound conforming to the structure of Formula (I) can be included in the composition in any suitable amount. Typically, the compound is present in the composition in an amount of about 50 parts-per-million (ppm) or more based on the weight of the organic material. Preferably, the compound is present in the composition in an amount of about 100 ppm or more, about 200 ppm or more, about 300 ppm or more, about 400 ppm or more, or about 500 ppm or more based on the weight of the organic material. The compound preferably is present in the composition in an amount of about 10,000 ppm or less, about 5,000 ppm or less, about 4,000 ppm or less, or about 3,000 ppm or less based on the weight of the organic material. Thus, in a series of preferred embodiments, the compound is present in the composition in an amount of about 50 ppm to about 10,000 ppm, about 100 ppm to about 5,000 ppm, about 100 ppm to about 4,000 ppm (e.g., about 200 ppm to about 4,000 ppm, about 300 ppm to about 4,000 ppm, about 400 ppm to about 4,000 ppm, or about 500 to about 4,000 ppm), or about 100 ppm to about 3,000 ppm (e.g., about 200 ppm to about 3,000 ppm, about 300 ppm to about 3,000 ppm, about 400 ppm to about 3,000 ppm, or about 500 to about 3,000 ppm) based on the weight of the organic material.

The composition of the invention can contain other additives in addition to the compound(s) conforming to the structure of Formula (I). The particular additives included in such compositions will depend, at least in part, on the particular host material (e.g., polymer) that is being stabilized or protected against oxidation. For example, when the polymer is a thermoplastic polymer, suitable additional polymer additives include, but are not limited to, antioxidants (e.g., phenolic antioxidants, phosphite antioxidants, and combinations thereof), anti-blocking agents (e.g., amorphous silica and diatomaceous earth), pigments (e.g., organic pigments and inorganic pigments) and other colorants (e.g., dyes and polymeric colorants), fillers and reinforcing agents (e.g., glass, glass fibers, talc, calcium carbonate, and magnesium oxysulfate whiskers), nucleating agents, clarifying agents, other acid scavengers (e.g., synthetic dihydrotalcite), polymer processing additives (e.g., fluoropolymer polymer processing additives), polymer cross-linking agents, slip agents (e.g., fatty acid amide compounds derived from the reaction between a fatty acid and ammonia or an amine-containing compound), fatty acid ester compounds (e.g., fatty acid ester compounds derived from the reaction between a fatty acid and a hydroxyl-containing compound, such as glycerol, diglycerol, and combinations thereof), and combinations of the foregoing.

As noted above, the composition of the invention can further comprise one or more antioxidants or stabilizer compounds (i.e., one or more antioxidants or stabilizer compounds in addition to the compound conforming to the structure of Formula (I)). For example, the composition can comprise a phenolic antioxidant (e.g., a hindered phenol compound), a phosphite antioxidant, a phosphonite antioxidant, or a suitable mixture of any of the foregoing. In one potentially preferred embodiment, the composition comprises a hindered phenol compound, with tetrakis[methylene-3-(3,5-di-tert-butyl-4-hydroxyphenyl)propionate]methane being a particularly preferred hindered phenol compound. In another potentially preferred embodiment, the composition comprises a stabilizer compound selected from the group consisting of phosphites, phosphonites, and mixtures thereof, with tris(2,4-di-tert-butylphenyl) phosphite being particularly preferred. In yet another potentially preferred embodiment, the composition comprises both a phenolic antioxidant (e.g., a hindered phenol compound) and a phosphite stabilizer compound. In a specific embodiment of such a composition, the composition further comprises both tetrakis[methylene-3-(3,5-di-tert-butyl-4-hydroxyphenyl)propionate]methane and tris(2,4-di-tert-butylphenyl)phosphite.

The following examples further illustrate the subject matter described above but, of course, should not be construed as in any way limiting the scope thereof.

EXAMPLE 1

This example demonstrates the synthesis of 3-(4-hydroxy-phenyl)-1-phenyl-1,3-dihydro-indole-2-one.

1-Phenyl oxindole (2.09 g, 0.01 mol, 1 equiv.) was dissolved in degassed dioxane in a pressure vessel. 4-Chlorophenol (1.29 g, 0.01 mol, 1 equiv.), potassium carbonate (4.2 g, 0.03 mol, 3 equiv.), Pd catalyst (0.1 g, 1 mol %), and XPhos (0.25 g, 5 mol %) were added to the solution. The solution was sparged with an argon blanket, sealed and heated for 24 h. After completion of the reaction, the reactor contents were neutralized and extracted in ethyl acetate. The solvent was stripped to obtain pure product as a white solid. The $^1$H nuclear magnetic resonance (NMR) spectrum of the product was taken in dimethyl sulfoxide. The spectrum exhibited the following peaks: 1H NMR ($\delta$, in DMSO): 4.6 (s, 1H), 6.7 (d, 2H), 6.9 (m, 4H), 7.2 (t, 2H), 9.4 (s, 1H), 10.4 (s, 1H).

EXAMPLE 2

This example demonstrates the synthesis of 3-(4-hexaethyleneglycol-phenyl)-1,3-dihydro-indole-2-one.

Oxindole (1.33 g, 0.01 mol, 1 equiv.) was dissolved in degassed dioxane in a pressure vessel. 4-Chlorophenol-6EO (4.89 g, 0.01 mol, 1 equiv.), potassium carbonate (4.2 g, 0.03 mol, 3 equiv.), Pd catalyst (0.1 g, 1 mol %), and XPhos (0.25 g, 5 mol %) were added to the solution. The solution was sparged with an argon blanket, sealed and heated for 24 h. After completion of the reaction, the reactor contents were neutralized and extracted in ethyl acetate. The solvent was stripped to obtain pure product as a white solid. The $^1$H nuclear magnetic resonance (NMR) spectrum of the product was taken in dimethyl sulfoxide. The spectrum exhibited the following peaks: $^1$H NMR ($\delta$, in DMSO): 3.2-3.5 (m, 20H), 3.6 (t, 2H), 3.8 (t, 2H) 4.5 (t, 1H), 4.6 (s, 1H), 6.7 (d, 2H), 6.9 (m, 4H), 7.2 (t, 2H), 10.4 (s, 1H).

EXAMPLE 3

This example demonstrates the synthesis of 3-(4-aminophenyl)-1,3-dihydro-indole-2-one.

Oxindole (1.33 g, 0.01 mol, 1 equiv.) was dissolved in degassed dioxane in a pressure vessel. 4-Chloroaniline (1.27 g, 0.01 mol, 1 equiv.), potassium carbonate (4.2 g, 0.03 mol, 3 equiv.), Pd catalyst (0.1 g, 1 mol %), XPhos (0.25 g, 5 mol %) were added to the solution. The solution was sparged with an argon blanket, sealed and heated for 24 h. After completion of the reaction, the reactor contents were neutralized and extracted in ethyl acetate. The solvent was stripped to obtain pure product as a white solid. The $^1$H nuclear magnetic resonance (NMR) spectrum of the product was taken in dimethyl sulfoxide. The spectrum exhibited the following peaks: $^1$H NMR (δ, in DMSO): 4.6 (s, 1H), 5.0 (brs, 2H), 6.7 (d, 2H), 6.9 (m, 4H), 7.2 (t, 2H), 10.4 (s, 1H).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the subject matter of this application (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the subject matter of the application and does not pose a limitation on the scope of the subject matter unless otherwise claimed. No language in the specification should be construed as indicating any non-claimed element as essential to the practice of the subject matter described herein.

Preferred embodiments of the subject matter of this application are described herein, including the best mode known to the inventors for carrying out the claimed subject matter. Variations of those preferred embodiments may become apparent to those of ordinary skill in the art upon reading the foregoing description. The inventors expect skilled artisans to employ such variations as appropriate, and the inventors intend for the subject matter described herein to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

What is claimed is:

1. A compound conforming to the structure of Formula (I)

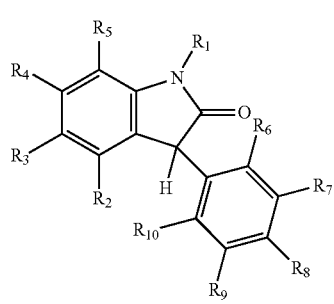

wherein $R_1$ is selected from the group consisting of hydrogen, alkyl groups, hydroxyalkyl groups, alkoxyalkyl groups, aryl groups, and $R_{20}$; $R_2$, $R_3$, $R_4$, and $R_5$ are independently selected from the group consisting of hydrogen, halogen atoms, alkyl groups, hydroxyalkyl groups, alkoxy groups, and aryl groups; $R_6$, $R_7$, $R_8$, $R_9$, and $R_{10}$ are independently selected from the group consisting of hydrogen, alkyl groups, alkoxy groups, aryl groups, $R_{14}$, $R_{15}$, —$SR_{16}$, —$NR_{17}R_{18}$, and —$OR_{20}$; provided if $R_1$ is selected from the group consisting of hydrogen, alkyl groups, hydroxyalkyl groups, alkoxyalkyl groups, aryl groups, alkanoyl groups, alkenoyl groups, and aryloyl groups, then at least one of $R_6$, $R_7$, $R_8$, $R_9$, and $R_{10}$ is selected from the group consisting of $R_{14}$, $R_{15}$, —$SR_{16}$, —$NR_{17}R_{18}$, and —$OR_{20}$; $R_{14}$ is a group conforming to the structure of Formula (II)

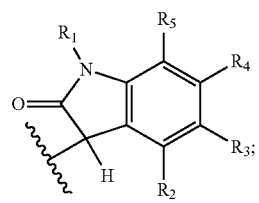

$R_{15}$ is a group conforming to the structure of Formula (III)

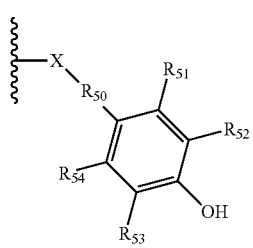

X is selected from the group consisting of —N(H)—, —O—C(O)—, and —N(H)—C(O)—; $R_{50}$ is selected from the group consisting of a bond and alkanediyl groups; $R_{51}$, $R_{52}$, $R_{53}$, and $R_{54}$ are independently selected from the group consisting of hydrogen and alkyl groups; $R_{16}$ is selected from the group consisting of hydrogen, alkyl groups, hydroxyalkyl groups, alkoxyalkyl groups, aryl groups, $R_{19}$, and $R_{20}$; $R_{19}$ is a group conforming to a structure selected from the group consisting of Formula (IVA), (IVB), and (IVC)

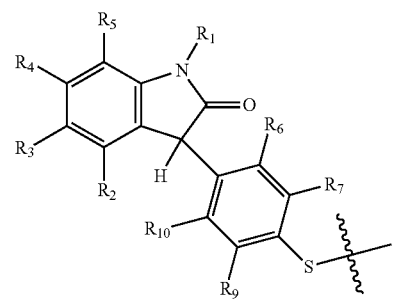

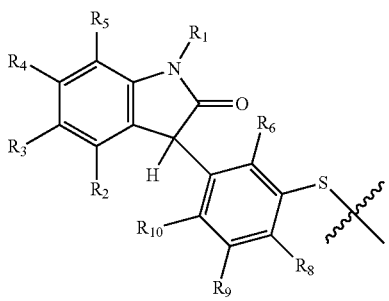

(IVB)

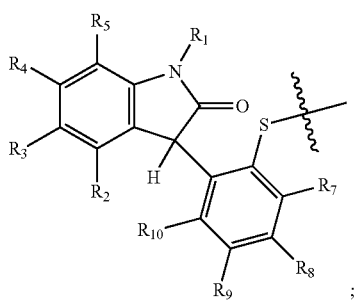

(IVC)

$R_{17}$ and $R_{18}$ are independently selected from the group consisting of hydrogen, alkyl groups, hydroxyalkyl groups, alkoxyalkyl groups, aryl groups, and $R_{20}$; and $R_{20}$ is selected from the group consisting of:

(a) alkanoyl groups, alkenoyl groups, and aryloyl groups;

(b) —$R_{21}$—O—$R_{22}$, where $R_{21}$ is selected from the group consisting of alkanediyl groups, and $R_{22}$ is selected from the group consisting of alkyl groups, alkanoyl groups, alkenoyl groups, and aryloyl groups;

(c) groups conforming to the structure of Formula (V)

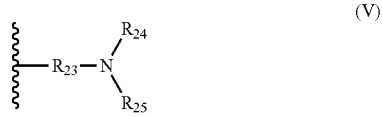

(V)

where $R_{23}$ is selected from the group consisting of alkanediyl groups, $R_{24}$ and $R_{25}$ are independently selected from the group consisting of hydrogen, alkyl groups, —$R_{21}$—O—$R_{22}$, —$R_{30}$—O—$R_{31}$—$R_{32}$, and —$R_{31}$—$R_{32}$;

(d) —$R_{30}$—O—$R_{31}$—$R_{32}$, where $R_{30}$ is selected from the group consisting of alkanediyl groups; and (e) —$R_{31}$—$R_{32}$, where $R_{32}$ is selected from the group consisting of hydrogen, alkyl groups, alkanoyl groups, alkenoyl groups, and aryloyl groups; and $R_{31}$ is a divalent substituent selected from the group consisting of:

(i) divalent substituents comprising two or more divalent repeating units independently selected from repeating units conforming to the structure of Formula (C)

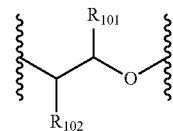

(C)

wherein $R_{101}$ and $R_{102}$ are independently selected from the group consisting of hydrogen, alkyl, hydroxyalkyl, aryl, alkoxyalkyl, and aryloxyalkyl;

(ii) divalent substituents conforming to the structure of Formula (CX)

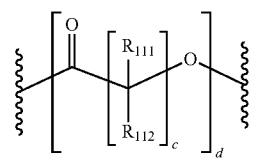

(CX)

wherein $R_{111}$ and $R_{112}$ are independently selected from the group consisting of hydrogen, hydroxyl, and $C_1$-$C_{10}$ alkyl, c is an integer from 1 to 12, and d is a positive integer;

(iii) divalent substituents conforming to the structure of Formula (CXX)

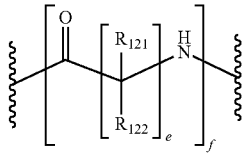

(CXX)

wherein $R_{121}$ and $R_{122}$ are independently selected from the group consisting of hydrogen, hydroxyl, and $C_1$-$C_{10}$ alkyl, e is an integer from 1 to 12, and f is a positive integer;

(iv) divalent substituents conforming to the structure of Formula (CXXX)

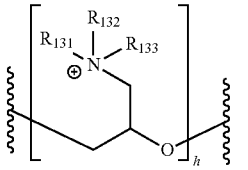

(CXXX)

wherein $R_{131}$, $R_{132}$, and $R_{133}$ are independently selected from alkyl and hydroxyalkyl, and h is a positive integer; and (v) divalent substituents comprising two or more substituents selected from the group consisting of substituents conforming to a structure of Formula (C), (CX), (CXX), or (CXXX).

2. The compound of claim 1, wherein at least one of $R_6$, $R_7$, $R_8$, $R_9$, and $R_{10}$ is —$OR_{20}$.

3. The compound of claim 2, wherein $R_{20}$ is selected from the group consisting of —$R_{30}$—O—$R_{31}$—$R_{32}$, and —$R_{31}$—$R_{32}$.

4. The compound of claim 3, wherein $R_{31}$ is a divalent substituent conforming to a structure selected from the group consisting of Formulae (CI), (CII), and (CIII)

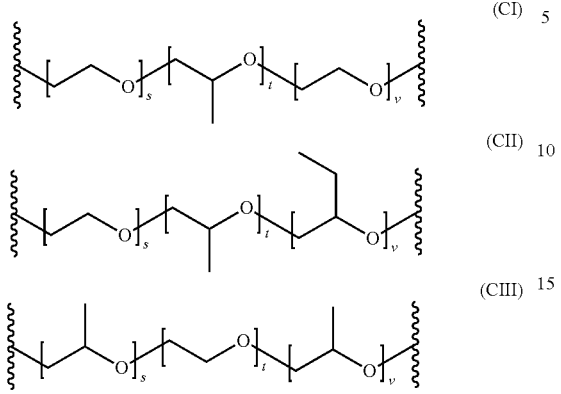

wherein s, t, and v are selected from the group consisting of zero and positive integers; and the sum of s, t, and v is 2 or more.

5. The compound of claim 4, wherein the sum of s, t, and v is from 2 to about 50.

6. The compound of claim 5, wherein $R_{31}$ is a divalent substituent conforming to the structure of Formula (CI), s is an integer from 2 to about 50, v is 0, and t is 0.

7. The compound of claim 6, wherein $R_8$ is —$OR_{20}$, and $R_6$, $R_7$, $R_9$, and $R_{10}$ are each hydrogen.

8. The compound of claim 7, wherein $R_1$, $R_2$, $R_3$, $R_4$, and $R_5$ are each hydrogen.

9. The compound of claim 8, wherein $R_{32}$ is hydrogen.

10. A composition comprising an organic material and a compound conforming to the structure of Formula (I)

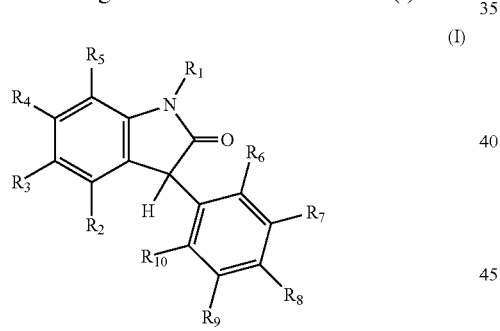

wherein $R_1$ is selected from the group consisting of hydrogen, alkyl groups, hydroxyalkyl groups, alkoxyalkyl groups, aryl groups, and $R_{20}$; $R_2$, $R_3$, $R_4$, and $R_5$ are independently selected from the group consisting of hydrogen, halogen atoms, alkyl groups, hydroxyalkyl groups, alkoxy groups, and aryl groups; $R_6$, $R_7$, $R_8$, $R_9$, and $R_{10}$ are independently selected from the group consisting of hydrogen, hydroxy, alkyl groups, alkoxy groups, aryl groups, $R_{14}$, $R_{15}$, —$SR_{16}$, —$NR_{17}R_{18}$, and —$OR_{20}$; $R_{14}$ is a group conforming to the structure of Formula (II)

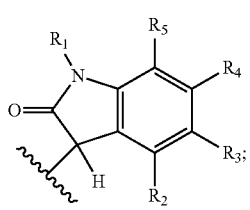

$R_{15}$ is a group conforming to the structure of Formula (III)

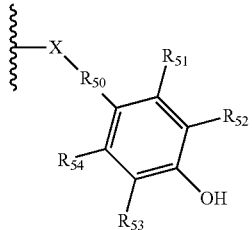

X is selected from the group consisting of —N(H)—, —O—C(O)—, and —N(H)—C(O)—; $R_{50}$ is selected from the group consisting of a bond and alkanediyl groups; $R_{51}$, $R_{52}$, $R_{53}$, and $R_{54}$ are independently selected from the group consisting of hydrogen and alkyl groups; $R_{16}$ is selected from the group consisting of hydrogen, alkyl groups, hydroxyalkyl groups, alkoxyalkyl groups, aryl groups, $R_{19}$, and $R_{20}$; $R_{19}$ is a group conforming to the structure of Formula (IVA), (IVB), or (IVC)

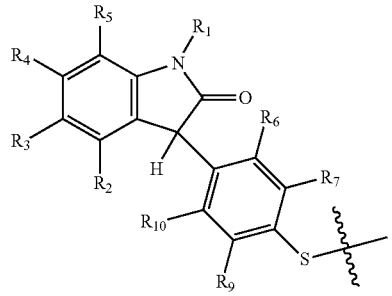

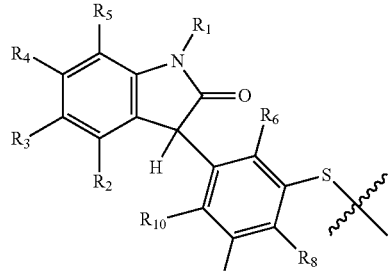

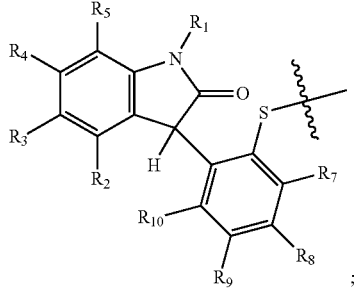

$R_{17}$ and $R_{18}$ are independently selected from the group consisting of hydrogen, alkyl groups, hydroxyalkyl groups, alkoxyalkyl groups, aryl groups, and $R_{20}$; and $R_{20}$ is selected from the group consisting of:
  (a) alkanoyl groups, alkenoyl groups, and aryloyl groups;
  (b) —$R_{21}$—O—$R_{22}$, where $R_{21}$ is selected from the group consisting of alkanediyl groups, and $R_{22}$ is selected from the group consisting of alkyl groups, alkanoyl groups, alkenoyl groups, and aryloyl groups;

(c) groups conforming to the structure of Formula (V)

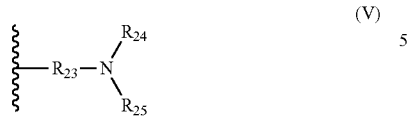

(V)

where $R_{23}$ is selected from the group consisting of alkanediyl groups, $R_{24}$ and $R_{25}$ are independently selected from the group consisting of hydrogen, alkyl groups, —$R_{21}$—O—$R_{22}$, —$R_{30}$—O—$R_{31}$—$R_{32}$, and —$R_{31}$—$R_{32}$;
(d) —$R_{30}$—O—$R_{31}$—$R_{32}$, where $R_{30}$ is selected from the group consisting of alkanediyl groups; and
(e) —$R_{31}$—$R_{32}$, where $R_{32}$ is selected from the group consisting of hydrogen, alkyl groups, alkanoyl groups, alkenoyl groups, and aryloyl groups; and $R_{31}$ is a divalent substituent selected from the group consisting of:
  (i) divalent substituents comprising two or more divalent repeating units independently selected from repeating units conforming to the structure of Formula (C)

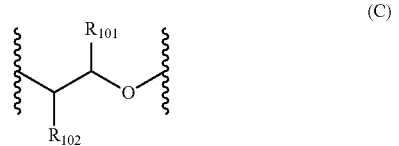

(C)

wherein $R_{101}$ and $R_{102}$ are independently selected from the group consisting of hydrogen, alkyl, hydroxyalkyl, aryl, alkoxyalkyl, and aryloxyalkyl;
  (ii) divalent substituents conforming to the structure of Formula (CX)

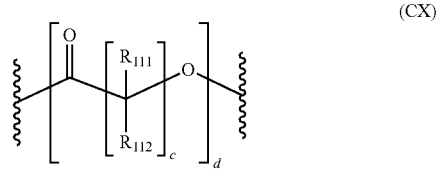

(CX)

wherein $R_{111}$ and $R_{112}$ are independently selected from the group consisting of hydrogen, hydroxyl, and $C_1$-$C_{10}$ alkyl, c is an integer from 1 to 12, and d is a positive integer;
  (iii) divalent substituents conforming to the structure of Formula (CXX)

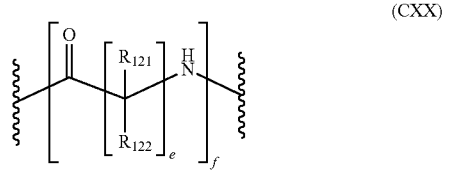

(CXX)

wherein $R_{121}$ and $R_{122}$ are independently selected from the group consisting of hydrogen, hydroxyl, and $C_1$-$C_{10}$ alkyl, e is an integer from 1 to 12, and f is a positive integer;

(iv) divalent substituents conforming to the structure of Formula (CXXX)

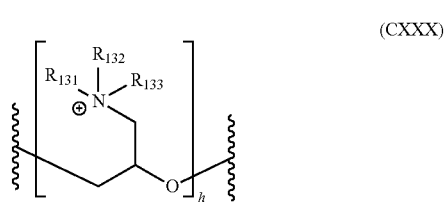

(CXXX)

wherein $R_{131}$, $R_{132}$, and $R_{133}$ are independently selected from alkyl and hydroxyalkyl, and h is a positive integer; and
  (v) divalent substituents comprising two or more substituents selected from the group consisting of substituents conforming to a structure of Formula (C), (CX), (CXX), or (CXXX).

11. The composition of claim 10, wherein the organic material is a thermoset polymer.

12. The composition of claim 11, wherein the organic material is a polyurethane polymer.

13. The composition of claim 10, wherein at least one of $R_6$, $R_7$, $R_8$, $R_9$, and $R_{10}$ is —$OR_{20}$.

14. The composition of claim 13, wherein $R_{20}$ is selected from the group consisting of —$R_{30}$—O—$R_{31}$—$R_{32}$, and —$R_{31}$—$R_{32}$.

15. The composition of claim 14, wherein $R_{31}$ is a divalent substituent conforming to a structure selected from the group consisting of Formulae (CI), (CII), and (CIII)

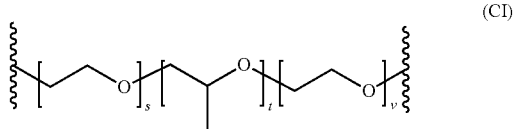

(CI)

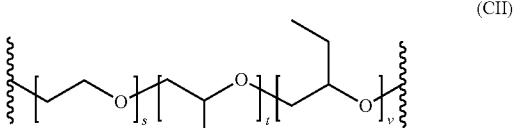

(CII)

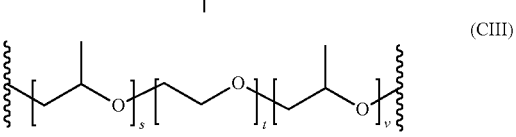

(CIII)

wherein s, t, and v are selected from the group consisting of zero and positive integers; and the sum of s, t, and v is 2 or more.

16. The composition of claim 15, wherein the sum of s, t, and v is from 2 to about 50.

17. The composition of claim 16, wherein $R_{31}$ is a divalent substituent conforming to the structure of Formula (CI), s is an integer from 2 to about 50, v is 0, and t is 0.

18. The composition of claim 17, wherein $R_8$ is —$OR_{20}$, and $R_6$, $R_7$, $R_9$, and $R_{10}$ are each hydrogen.

19. The composition of claim 18, wherein $R_1$, $R_2$, $R_3$, $R_4$, and $R_5$ are each hydrogen.

20. The composition of claim 19, wherein $R_{32}$ is hydrogen.

* * * * *